(12) United States Patent
Larson et al.

(10) Patent No.: US 10,596,295 B2
(45) Date of Patent: Mar. 24, 2020

(54) ADHESIVE PATCH ARRANGEMENT FOR A PHYSIOLOGICAL CHARACTERISTIC SENSOR, AND RELATED SENSOR ASSEMBLY

(71) Applicant: MEDTRONIC MINIMED, INC., Northridge, CA (US)

(72) Inventors: Eric Allan Larson, Simi Valley, CA (US); Voltaire Isaac Lebron, Camarillo, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 181 days.

(21) Appl. No.: 15/688,596

(22) Filed: Aug. 28, 2017

(65) Prior Publication Data

US 2019/0060511 A1     Feb. 28, 2019

(51) Int. Cl.
| | |
|---|---|
| *A61B 5/00* | (2006.01) |
| *A61L 15/58* | (2006.01) |
| *A61B 5/145* | (2006.01) |
| *A61B 5/1486* | (2006.01) |

(52) U.S. Cl.
CPC .......... *A61L 15/58* (2013.01); *A61B 5/14532* (2013.01); *A61B 5/14865* (2013.01); *A61B 5/6833* (2013.01); *A61B 5/6849* (2013.01)

(58) Field of Classification Search
CPC ... A61B 5/683; A61B 5/6833; A61B 5/68335; A61B 5/14532; A61B 5/1477; A61B 5/6801; A61B 5/6813; A61L 15/58
See application file for complete search history.

(56) References Cited

U.S. PATENT DOCUMENTS

| | | | |
|---|---|---|---|
| 4,755,173 | A | 7/1988 | Konopka et al. |
| 5,391,250 | A | 2/1995 | Cheney, II et al. |
| 5,485,408 | A | 1/1996 | Blomquist |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |

(Continued)

*Primary Examiner* — Max F Hindenburg
(74) *Attorney, Agent, or Firm* — Lorenz & Kopf, LLP (57) ABSTRACT

An adhesive patch arrangement for a sensor includes a flexible patch, a sensor-affixing feature located in a sensor mounting region of the component-facing side of the flexible patch, the sensor-affixing feature securing the sensor to the flexible patch, and a device-affixing feature located in a device mounting region of the component-facing side of the flexible patch. The device-affixing feature secures a device to the flexible patch. The sensor mounting and device mounting regions are distinct and separate regions. The arrangement also includes a removable reinforcement liner adhered to, and covering, the device-affixing feature, and shaped to define a cutout area that partially surrounds the sensor-affixing feature. The arrangement also includes a removable backing liner adhered to, and covering, the adhesive skin-facing side of the flexible adhesive patch.

20 Claims, 10 Drawing Sheets

(56) References Cited

U.S. PATENT DOCUMENTS

| | | |
|---|---|---|
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,892,085 B2 | 5/2005 | Melvor et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,468,033 B2 | 12/2008 | Van Antwerp et al. |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,845,536 B2 * | 9/2014 | Brauker ............ A61B 5/150022 600/365 |
| 8,864,664 B2 * | 10/2014 | Frey .................... A61B 5/14532 600/300 |
| 8,965,498 B2 * | 2/2015 | Katra ................... A61B 5/0537 600/547 |
| 9,014,778 B2 * | 4/2015 | Datta ....................... A61B 5/06 600/372 |
| 9,101,305 B2 | 8/2015 | Larson et al. |
| 9,451,897 B2 * | 9/2016 | Mazar ................ A61B 5/04085 |
| 9,782,132 B2 * | 10/2017 | Golda ................ A61B 5/04325 |
| 10,004,421 B2 * | 6/2018 | Gilmore ............... A61B 5/6833 |
| 10,070,820 B2 * | 9/2018 | Huang ................... A61B 5/685 |
| 10,117,608 B2 * | 11/2018 | Poulsen ............. A61B 5/14542 |
| 2007/0123819 A1 | 5/2007 | Mernoe et al. |
| 2009/0299301 A1 | 12/2009 | Gottlieb et al. |
| 2010/0160861 A1 | 6/2010 | Causey, III et al. |
| 2013/0178725 A1 * | 7/2013 | O'Neil ............... A61B 5/68335 600/324 |
| 2014/0336486 A1 * | 11/2014 | Ouyang ............. A61B 5/14532 600/347 |
| 2015/0087951 A1 * | 3/2015 | Felix .................. A61B 5/04085 600/382 |
| 2016/0287148 A1 * | 10/2016 | Pizer ................... A61B 5/7475 |

\* cited by examiner

ADHESIVE PATCH ARRANGEMENT FOR A PHYSIOLOGICAL CHARACTERISTIC SENSOR, AND RELATED SENSOR ASSEMBLY

TECHNICAL FIELD

Embodiments of the subject matter described herein relate generally to medical devices and related manufacturing and assembly techniques. More particularly, embodiments of the subject matter relate to a physiological characteristic sensor product that is designed to be temporarily adhered to the body of a patient.

BACKGROUND

The prior art includes a wide variety of medical devices and components, related manufacturing techniques, and related packaging techniques. For example, physiological characteristic sensors are generally known in the art for use in a variety of specialized applications. In this regard, thin film electrochemical sensors are used to test analyte levels in patients. More specifically, thin film sensors have been designed for use in obtaining an indication of blood glucose (BG) levels and monitoring BG levels in a diabetic patient, with the distal segment portion of the sensor positioned subcutaneously in direct contact with patient extracellular fluid. Such readings can be especially useful in adjusting a treatment regimen which typically includes regular administration of insulin to the patient.

A glucose sensor of the type described above may be packaged and sold as an assembled product that includes certain features or components that allow the patient to position and subcutaneously implant the sensor. For example, thin film glucose sensors are often implanted subcutaneously/transcutaneously using a needle that punctures the skin of the patient as the sensor is introduced. The glucose sensor product may include the sensor device mounted to a flexible adhesive skin patch, which in turn is mounted on a pedestal (that is utilized for storing and shipping the product). The glucose sensor product may also include a removable needle hub that contains the insertion needle. The glucose sensor product is compatible with an insertion device that cooperates with the needle hub to insert the needle. A subcutaneous glucose sensor of this type is sensitive to placement and positioning on the skin. Accordingly, it is important to take good care when deploying the glucose sensor product to ensure successful adhesion of the mounting patch to the patient's skin.

BRIEF SUMMARY

An adhesive patch arrangement for a physiological characteristic sensor is disclosed herein. An embodiment of the adhesive patch arrangement includes: a flexible adhesive patch having an adhesive skin-facing side, and a component-facing side opposite the adhesive skin-facing side; a sensor-affixing feature located in a sensor mounting region of the component-facing side of the flexible adhesive patch, the sensor-affixing feature having an adhesive sensor-receiving surface to secure the physiological characteristic sensor to the flexible adhesive patch; a device-affixing feature located in a device mounting region of the component-facing side of the flexible adhesive patch, the device-affixing feature having an adhesive device-receiving surface to secure a device to the flexible adhesive patch, wherein the sensor mounting region and the device mounting region are distinct and separate regions; a removable reinforcement liner adhered to, and covering, the adhesive device-receiving surface of the device-affixing feature, the reinforcement liner being shaped to define a cutout area that at least partially surrounds the sensor-affixing feature, and the reinforcement liner being formed from a material that reinforces structural rigidity of the flexible adhesive patch when the reinforcement liner is adhered to the adhesive device-receiving surface; and a removable backing liner adhered to, and covering, the adhesive skin-facing side of the flexible adhesive patch.

A physiological characteristic sensor assembly is also disclosed herein. An embodiment of the sensor assembly includes: a transport pedestal having a mounting surface; a backing liner having a patch-facing side and a pedestal-facing side opposite the patch-facing side, wherein at least a portion of the pedestal-facing side is attached to the mounting surface of the transport pedestal; a flexible adhesive patch having an adhesive skin-facing side removably adhered to the patch-facing side of the backing liner, and having a component-facing side opposite the adhesive skin-facing side; a physiological characteristic sensor coupled to a sensor mounting region of the component-facing side of the flexible adhesive patch; a device-affixing feature located in a device mounting region of the component-facing side of the flexible adhesive patch, the device-affixing feature having an adhesive device-receiving surface to secure a device to the flexible adhesive patch, wherein the sensor mounting region and the device mounting region are distinct and separate regions; and a removable reinforcement liner adhered to the adhesive device-receiving surface of the device-affixing feature, the removable reinforcement liner being shaped to define a cutout area that at least partially flanks the physiological characteristic sensor, and the removable reinforcement liner being formed from a material that reinforces structural rigidity of the flexible adhesive patch.

An embodiment of the physiological characteristic sensor assembly includes: a transport pedestal having a primary mounting surface; an adhesive patch arrangement as summarized above, wherein the removable backing liner of the adhesive patch arrangement is coupled to the primary mounting surface of the transport pedestal; and a glucose sensor coupled to the flexible adhesive patch of the adhesive patch arrangement by way of the sensor-affixing feature.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology and descriptors may be used in the following description for the purpose of reference only, and thus are not intended to be limiting. For example, terms such as "upper," "lower," "above," and "below" refer to directions in the drawings to which reference is made. Terms such as "front," "back," "rear," "side," "outboard," and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first," "second," and other such numerical terms referring to structures do not imply a sequence or order unless clearly indicated by the context.

The subject matter described here relates to the manufacturing and assembly of a physiological characteristic sensor product. The non-limiting exemplary embodiment described below relates to a continuous glucose sensor of the type used by diabetic patients. It should be appreciated that the concepts, manufacturing and packaging techniques, and components mentioned here need not be limited to use with glucose sensors and, indeed, the concepts and technology described with reference to a glucose sensor could also be used with other medical devices, other physiological characteristic sensor types, other medical components or supplies, and the like.

For the sake of brevity, conventional aspects and technology related to glucose sensors and glucose sensor fabrication may not be described in detail here. A glucose sensor of the type described here may be realized as an electrochemical sensor that employs the glucose oxidase enzyme. Sensors that use glucose oxidase to effect a reaction of glucose and oxygen are known, and such glucose sensors will not be described in detail here. In this regard, known and/or conventional aspects of glucose sensors and their manufacturing may be of the type described in, but not limited to: U.S. Pat. Nos. 6,892,085 and 7,468,033, and U.S. patent application number 2009/0299301 (which are incorporated by reference herein).

Figure 1:
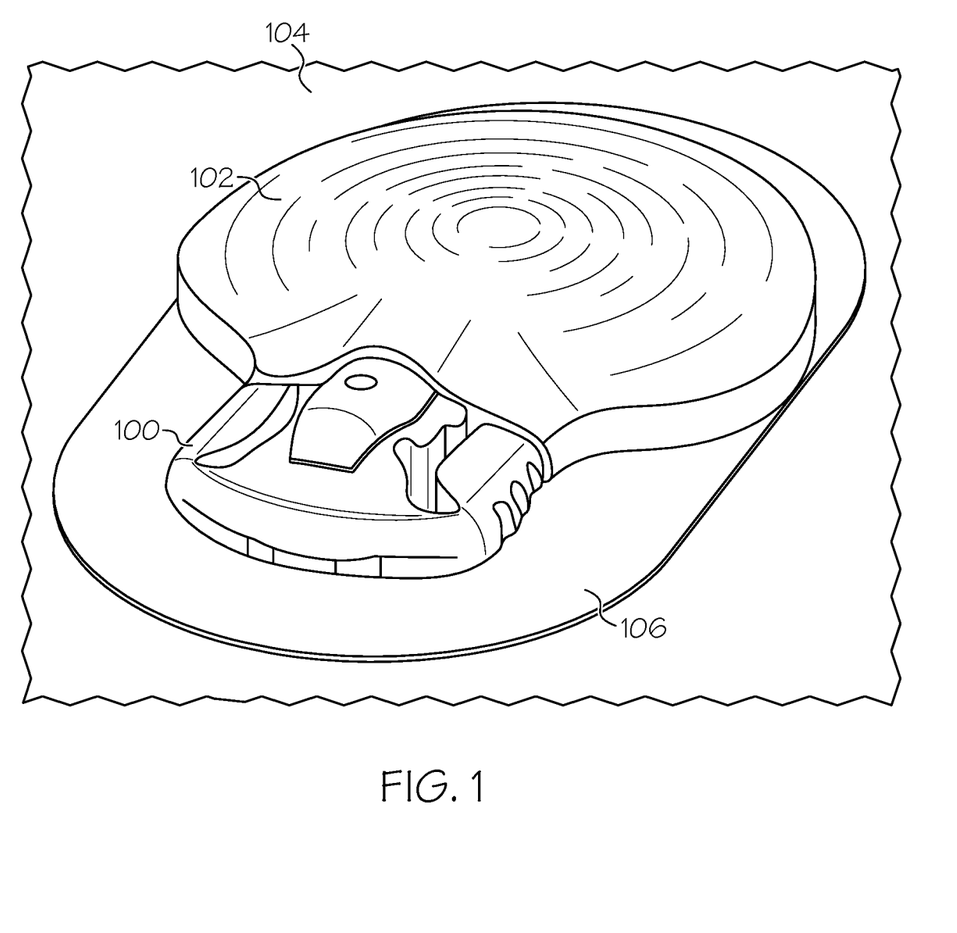
FIG. 1 is a perspective view of an exemplary embodiment of a glucose sensor and its wireless transmitter affixed to the skin of a patient.

FIG. 1 is a perspective view of an exemplary embodiment of a physiological characteristic sensor 100 and its wireless transmitter 102 affixed to the skin 104 of a patient. The sensor 100 and the wireless transmitter 102 are affixed to the skin 104 by way of a flexible adhesive patch 106. The sensor 100 and the wireless transmitter 102 include certain features that allow the wireless transmitter 102 to be removably coupled (physically and electrically) to the sensor 100, as shown in FIG. 1. The sensor 100 and the adhesive patch 106 are designed and intended to be disposables to be replaced after several days of continuous use. In contrast, the wireless transmitter 102 is designed and intended to be a durable assembly that can be removed from the sensor 100, recharged as needed, and reused a number of times with replacement sensors 100. In accordance with the illustrated embodiment, the sensor 100 and the flexible adhesive patch 106 are deployed in a single step. Thereafter, the wireless transmitter 102 is connected to the sensor 100 and secured to the top side of the flexible adhesive patch 106. FIG. 1 depicts the assembly after the wireless transmitter 102 has been secured to the flexible adhesive patch 106.

Figure 2:
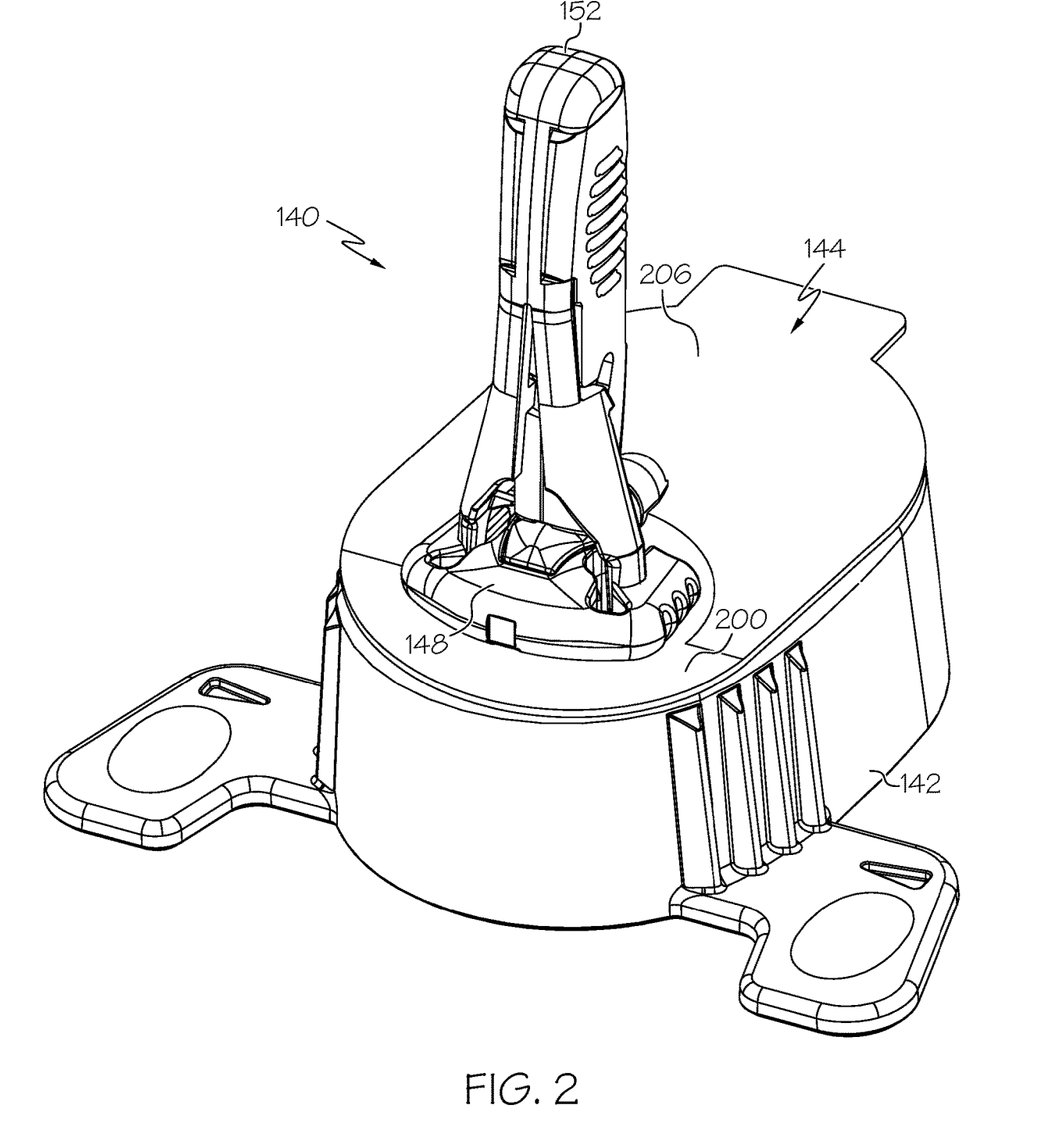
FIG. 2 is a perspective view of an exemplary embodiment of a glucose sensor product.
Figure 3:
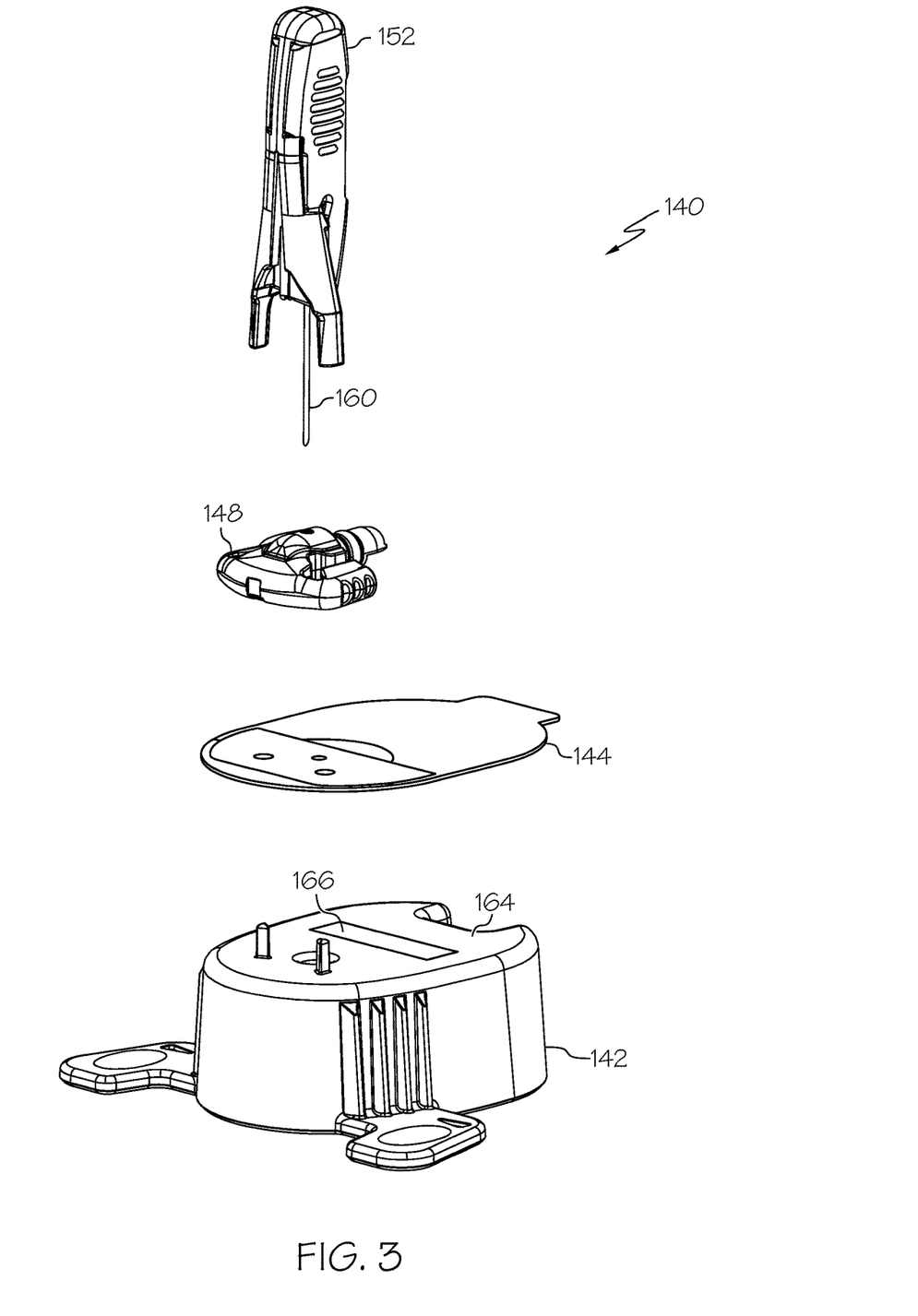
FIG. 3 is an exploded perspective view of the glucose sensor product shown in FIG. 2.

As mentioned above, a continuous glucose sensor is one exemplary implementation of a physiological characteristic sensor of the type contemplated by this disclosure. In this regard, FIG. 2 is a perspective view of an exemplary embodiment of a glucose sensor product 140, and FIG. 3 is an exploded perspective view of the glucose sensor product 140. The glucose sensor product 140 is an assembled item that can be packaged in an appropriate manner for delivery and use by a caregiver, the patient, etc. For example, the glucose sensor product 140 can be packaged together in a sealed tray with a removable lid, such as that shown in U.S. Pat. No. 9,101,305.

With continued reference to FIG. 2 and FIG. 3, the illustrated embodiment of the glucose sensor product 140 generally includes, without limitation: a transport pedestal 142; an adhesive patch arrangement 144; a glucose sensor 148; and a needle hub assembly 152. As depicted in FIG. 2, the components of the glucose sensor product 140 are coupled together as a single unit for packaging. Many features, aspects, and characteristics of the glucose sensor product 140 and its individual elements are conventional and, as such, will not be described in detail here.

The transport pedestal 142 receives and protects an insertion needle 160 of the needle hub assembly 152 during packaging, shipping, and handling before deployment of the glucose sensor 148. The transport pedestal 142 provides a sturdy protective platform for the glucose sensor product 140, and it can support the various components during assembly, packaging, shipping, and storage. The transport pedestal 142 includes a primary mounting surface 164 (shown in FIG. 3, but hidden from view in FIG. 2) for the other components of the glucose sensor product 140. The primary mounting surface 164 shaped and sized to accommodate the shape and size of the adhesive patch arrangement 144.

During assembly of the glucose sensor product 140, the adhesive patch arrangement 144 is coupled to the primary mounting surface 164 of the transport pedestal 142 in the desired position (see FIG. 2). More specifically, a removable backing liner of the adhesive patch arrangement 144 is affixed to the primary mounting surface 164 of the transport pedestal 142. The removable backing liner (which is described in more detail below with reference to FIG. 4) can be attached to the primary mounting surface 164 using an adhesive material, double-sided tape, glue, or the like. The illustrated embodiment utilizes a strip of double-sided adhesive tape 166 to secure the removable backing liner in place on the transport pedestal 142.

Figure 4:
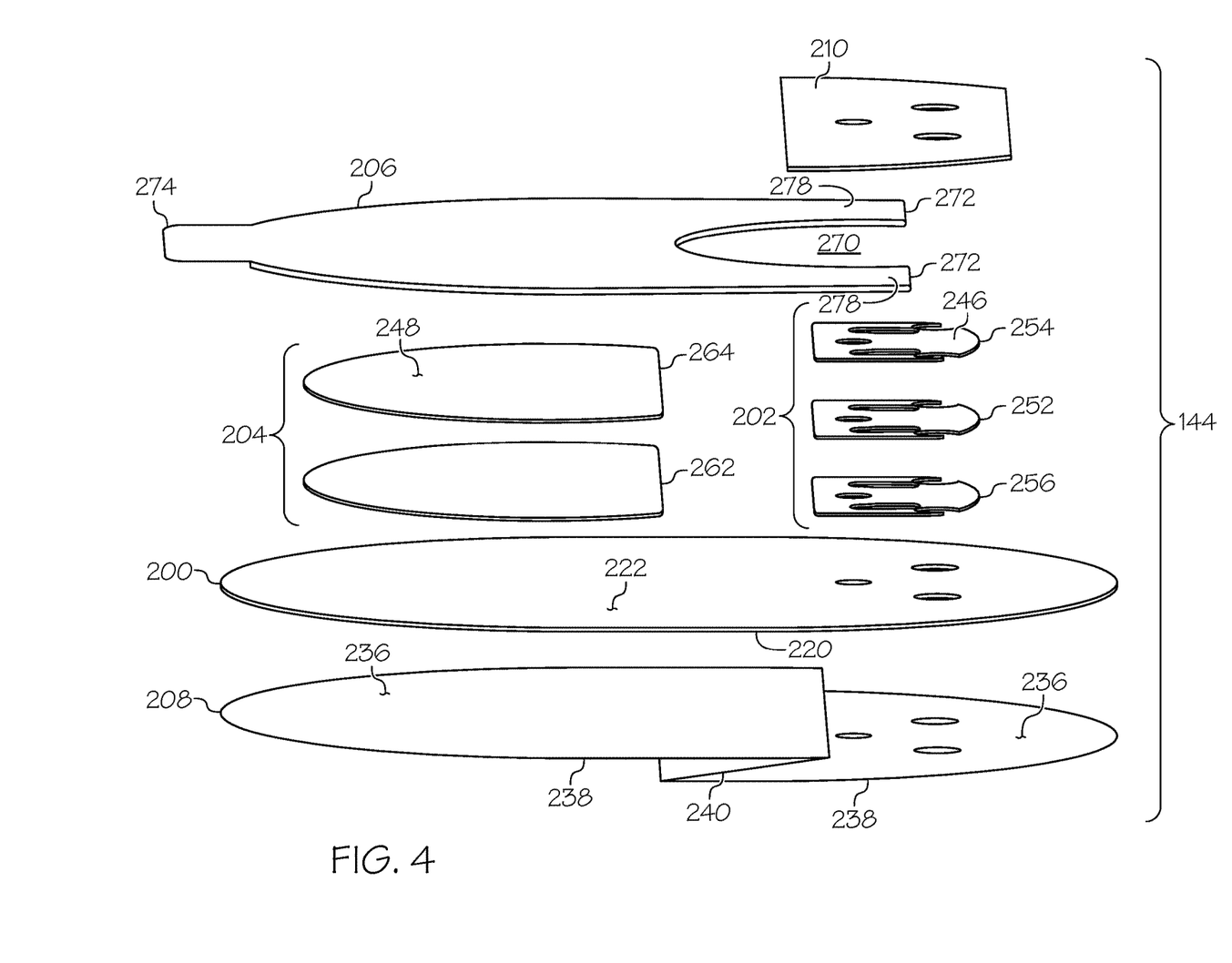
FIG. 4 is an exploded perspective view of an exemplary embodiment of an adhesive patch arrangement suitable for use with the glucose sensor product shown in FIG. 2.
Figure 5:
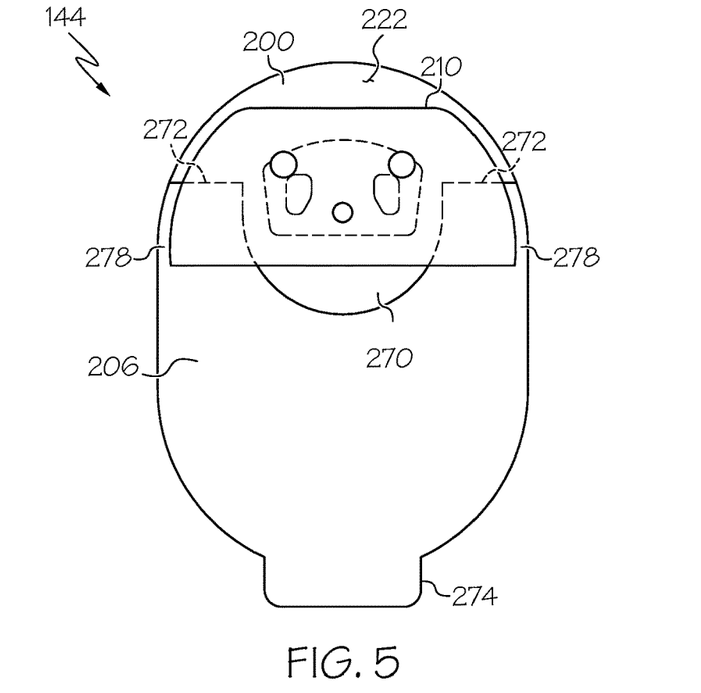
FIG. 5 is a top view of the adhesive patch arrangement shown in FIG. 4.
Figure 6:
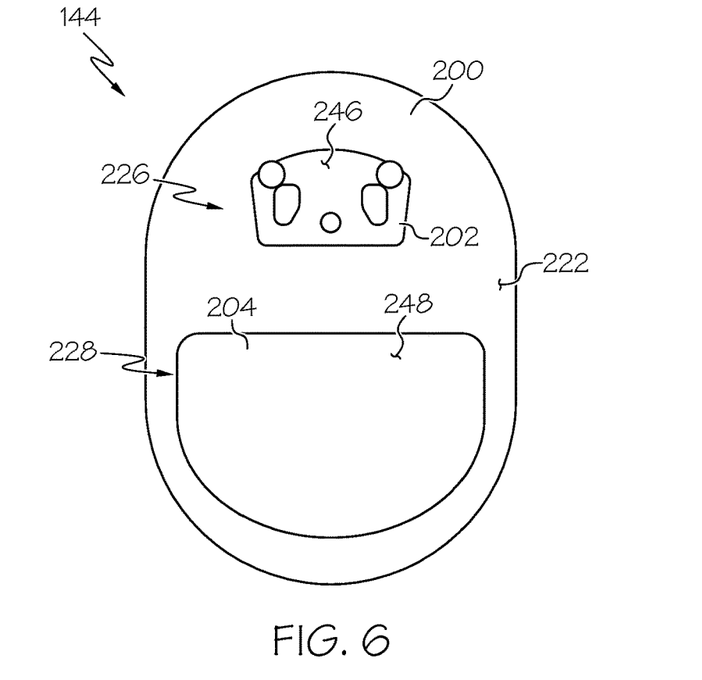
FIG. 6 is a top view of a portion of the adhesive patch arrangement shown in FIG. 4.

FIG. 4 is an exploded perspective view of an exemplary embodiment of the adhesive patch arrangement 144, FIG. 5 is a top view of the adhesive patch arrangement 144, and FIG. 6 is a top view of a portion of the adhesive patch arrangement 144. The illustrated embodiment of the adhesive patch arrangement 144 includes, without limitation: a flexible adhesive patch 200; a sensor-affixing feature 202; a device-affixing feature 204; a removable reinforcement liner 206; a removable backing liner 208; and a removable release liner 210. The adhesive patch arrangement 144 can be provided as a pre-manufactured unit for use during assembly of the glucose sensor product 140.

The flexible adhesive patch 200 serves to affix the glucose sensor 148 to the skin of the patient. The flexible adhesive patch 200 is preferably formed from a flexible and breathable material with adhesive properties, such as cloth, a bandage-like material, or the like. For example, suitable materials could include polyurethane, polyethylene, polyester, polypropylene, polytetrafluoroethylene (PTFE), or other polymers. The flexible adhesive patch 200 has an adhesive skin-facing side 220 and a component-facing side 222 that is opposite the adhesive skin-facing side 220. The component-facing side 222 includes a sensor mounting region 226 and a device mounting region 228 (see FIG. 6). For the embodiment described here, the sensor mounting region 226 and the device mounting region 228 are two distinct and separate regions located on the component-facing side 222. For example, the sensor mounting region 226 can be located at or near one end of the flexible adhesive patch 200, and the device mounting region 228 can be located at or near the opposite end of the flexible adhesive patch 200.

The removable backing liner 208 is adhered to, and covers, the adhesive skin-facing side 220 of the flexible adhesive patch 200. A patch-facing side 236 of the removable backing liner 208 is releasably affixed to the adhesive skin-facing side 220 of the flexible adhesive patch 200, such that the adhesive skin-facing side 220 is exposed when the removable backing liner 208 is separated from the flexible adhesive patch 200. The removable backing liner 208 has a pedestal-facing side 238 opposite the patch-facing side 236. As mentioned above with reference to FIG. 3, at least a portion of a pedestal-facing side 238 of the removable backing liner 208 can be attached to the mounting surface 164 of the transport pedestal 142 (by way of the adhesive tape 166) to secure the adhesive patch arrangement 144 to the transport pedestal 142. In practice, the adhesive tape 166 is strong enough to retain the removable backing liner 208 on the transport pedestal 142 after separation from the flexible adhesive patch 200.

In accordance with the illustrated embodiment, the removable backing liner 208 includes at least one fold 240 formed therein. More specifically, the at least one fold 240 is implemented as a z-fold section, as shown in FIG. 4. The at least one fold 240 is designed to facilitate peeling removal of the removable backing liner 208 from the adhesive skin-facing side of the flexible adhesive patch 200. In other words, the at least one fold 240 enables quick and easy separation of the flexible adhesive patch 200 from the transport pedestal 142 as intended. In practice, peeling is preferred over other separation methods such as cleavage, shear, and tensile because peeling will have the lowest force in this use case, which makes it easier for the patient. Moreover, the removable backing liner 208 is designed to peel easily enough such that the reinforcement liner 206 retains its shape and position and is not overpowered (e.g., folded or crimped) by the peeling force required to remove the removable backing liner 208. In addition, the placement of the z-fold section is selected such that the fold lies at or near a centered hole that accommodates the needle. Without the z-fold, the needle would interfere with the bottom liner and possibly damage the needle. In accordance with the exemplary embodiment shown here, the total fold lengths are longer than the needle so the needle is clear of the hole prior to peeling off the removable backing liner 208.

With continued reference to FIG. 4 and FIG. 6, the sensor-affixing feature 202 is located in the sensor mounting region 226 of the flexible adhesive patch 200, and the device-affixing feature 204 is located in the device mounting region 228 of the flexible adhesive patch 200. The sensor-affixing feature 202 can be implemented using a curable adhesive material, glue, a bonding agent, an adhesive component or device, or the like. In certain embodiments, the sensor-affixing feature 202 has an adhesive sensor-receiving surface 246 that is used to secure the glucose sensor 148 to the sensor mounting region 226 of the flexible adhesive patch 200. To this end, the adhesive sensor-receiving surface 246 of the sensor-affixing feature 202 is appropriately shaped and sized to accommodate the glucose sensor 148. Similarly, the device-affixing feature 204 has an adhesive device-receiving surface 248 that is used to secure a device (such as the wireless transmitter 102 shown in FIG. 1) to the device mounting region 228 of the flexible adhesive patch 200. In accordance with the illustrated embodiment, the adhesive device-receiving surface 248 of the device-affixing feature 204 is appropriately shaped and sized to accommodate a wireless transmitter for the glucose sensor 148.

Although not always required, the illustrated embodiment of the sensor-affixing feature 202 is realized as a double-sided adhesive element (see FIG. 4). For this particular embodiment, the sensor-affixing feature 202 is implemented as a multilayer component having a substrate layer 252, a first adhesive layer 254, and a second adhesive layer 256. The substrate layer 252 has an upper surface and a lower surface, the first adhesive layer 254 is formed on (or resides on) the upper surface, and the second adhesive layer 256 is formed on (or resides on) the lower surface. The second adhesive layer 256 is directly coupled to the flexible adhesive patch 200, and the substrate layer 252 is sandwiched between the two adhesive layers 254, 256. Thus, the second adhesive layer 256 couples the substrate layer 252 to the component-facing side 222 of the flexible adhesive patch 200. During assembly of the glucose sensor product 140, the glucose sensor 148 is directly affixed to the first adhesive layer 254. The substrate layer 252 provides structural rigidity to the sensor-affixing feature 202, which is helpful to strengthen the bond that is eventually created between the flexible adhesive patch 200 and the glucose sensor 148. Ideally, this bond is "permanent" in nature such that the glucose sensor 148 remains on the flexible adhesive patch 200 during shipping, deployment, and removal from the skin of the patient. The lamination technique utilized to fabricate the sensor-affixing feature 202 makes the sensor product less expensive to produce by making it easier to assemble the sensor onto the base. In this regard, competing wet processes, such as the use of epoxy, are more cumbersome to work with—a patch laminated with double sided adhesive elements in appropriate locations simplifies the supply chain.

The device-affixing feature 204 can be implemented using a curable adhesive material, glue, a bonding agent, an adhesive component or device, or the like. Although not always required, the illustrated embodiment of the device-affixing feature 204 is realized as a double-sided adhesive element (see FIG. 4). For this particular embodiment, the device-affixing feature 204 is implemented as a multilayer component having a first adhesive layer 262 and a second adhesive layer 264. The first adhesive layer 262 is coupled to the component-facing side 222 of the flexible adhesive patch 200, and the second adhesive layer 264 is coupled to the first adhesive layer 262. In accordance with the exemplary embodiment described here, the first adhesive layer 262 is realized as a single use adhesive layer that is intended to be "permanently" bonded to the component-facing side 222. In contrast, the second adhesive layer 264 is preferably realized as a multiple use adhesive layer to facilitate repeated installations and removals of a durable component, e.g., the wireless transmitter 102 for the glucose sensor 148.

FIG. 6 is a top view of the adhesive patch arrangement 144 after the sensor-affixing feature 202 and the device-affixing feature 204 have been applied to the flexible adhesive patch 200. During fabrication of the adhesive patch arrangement 144, the removable reinforcement liner 206 is adhered to the adhesive device-receiving surface 248 of the device-affixing feature 204, such that the reinforcement liner 206 covers and protects the adhesive device-receiving surface 248. Thereafter, the removable release liner 210 is adhered to the adhesive sensor-receiving surface 246 of the sensor-affixing feature 202, such that the release liner 210 covers and protects the adhesive sensor-receiving surface 246. FIG. 5 depicts a top view of the adhesive patch arrangement 144 after the reinforcement liner 206 and the release liner 210 have been installed. Notably, when properly installed as shown in FIG. 5, the release liner 210 covers and overlaps a portion of the reinforcement liner 206. More specifically, the release liner 210 covers at least a portion of the reinforcement liner 206 that defines a cutout area 270, wherein the cutout area 270 at least partially surrounds the sensor-affixing feature 202.

In accordance with certain embodiments, the removable reinforcement liner 206 includes at least one fold 272 formed therein to facilitate peeling removal of the reinforcement liner 206 from the adhesive device-receiving surface 248 of the device-affixing feature 204. The illustrated embodiment of the reinforcement liner 206 also includes a pull tab 274 to initiate removal of the reinforcement liner 206 from the device-affixing feature 204. As explained in more detail below, the reinforcement liner 206 is removed after the flexible adhesive patch 200 has been affixed to the skin of the patient, such that the wireless transmitter can be installed and connected to the glucose sensor 148.

The reinforcement liner 206 is formed from a suitable material that reinforces the structural rigidity of the flexible adhesive patch 200 when the reinforcement liner is adhered to the adhesive device-receiving surface 248. In this regard, the reinforcement liner 206 has a stiffness measurement that exceeds the stiffness measurement of the flexible adhesive patch 200. As explained in more detail below, the stiffness of the reinforcement liner 206 is desirable to reduce or eliminate unwanted drooping, bending, creasing, wrinkling, or folding of the flexible adhesive patch 200 during deployment of the glucose sensor 148.

In accordance with an exemplary manufacturing process, the fabricated adhesive patch arrangement 144 is affixed to the mounting surface of the transport pedestal 142 during assembly of the glucose sensor product 140. After securing the adhesive patch arrangement 144 onto the transport pedestal 142, the release liner 210 is removed from the sensor-affixing feature 202 to expose the adhesive sensor-receiving surface 246. The glucose sensor 148 is affixed to the exposed adhesive sensor-receiving surface 246 to secure it in place on the flexible adhesive patch 200, and the needle hub assembly 152 is removably coupled to the glucose sensor 148 (as shown in FIG. 2). The glucose sensor 148 remains coupled to the sensor mounting region 226 of the flexible adhesive patch 200. The reinforcement liner 206 remains in place on the flexible adhesive patch 200 until the glucose sensor is deployed on the skin of the patient. The cutout area 270 defined by the reinforcement liner 206 flanks at least a portion of the sensor-affixing feature 202 and, consequently, surrounds at least a portion of the glucose sensor 148, as shown in FIG. 2. As shown in FIG. 4 and FIG. 5, the reinforcement liner 206 terminates at two arm sections 278 on either side of the sensor-affixing feature 202. The cutout area 270 is particularly shaped to avoid tearing the reinforcement liner 206 during removal. As depicted in the figures, the cutout area 270 resembles the shape of an egg, or oval in shape. The cutout area 270 is intentionally designed to avoid sharp transitions and corners, which could promote tearing when the user peels the reinforcement liner 206 off.

Figure 7:
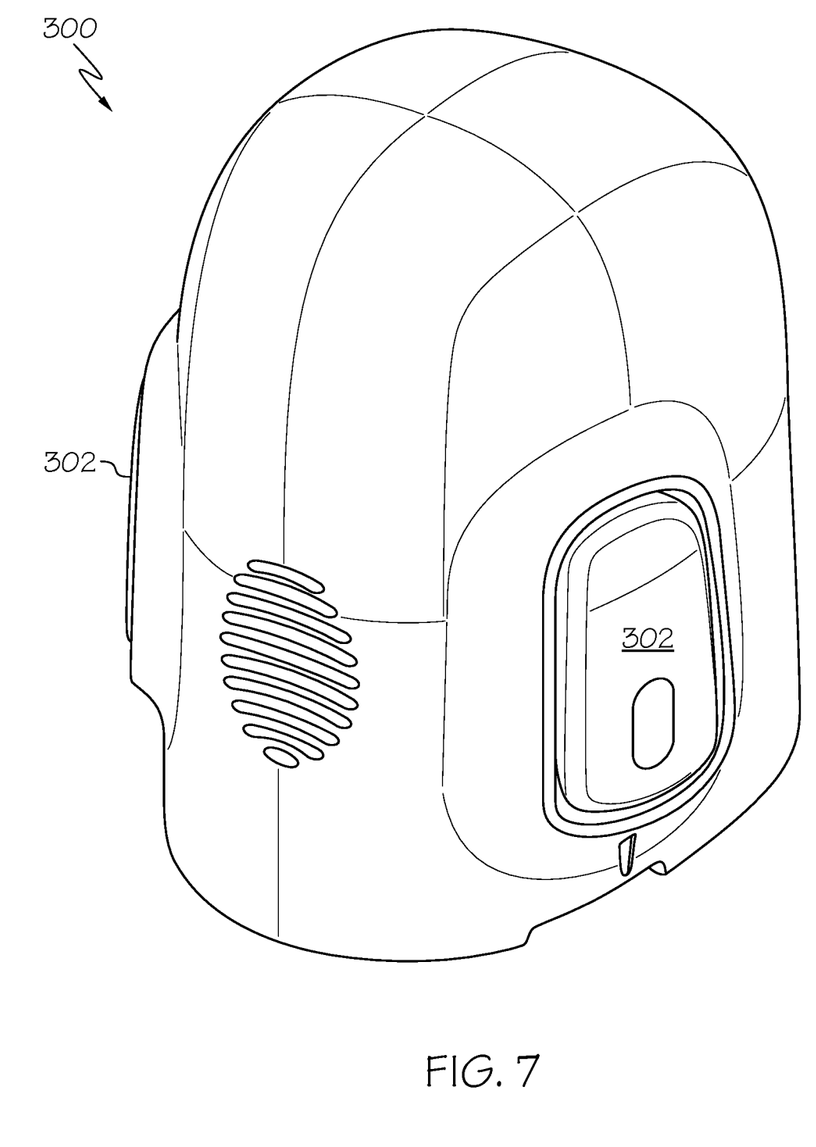
FIG. 7 is a perspective view of an insertion device that can be used with the glucose sensor product shown in FIG. 2.
Figure 8A:
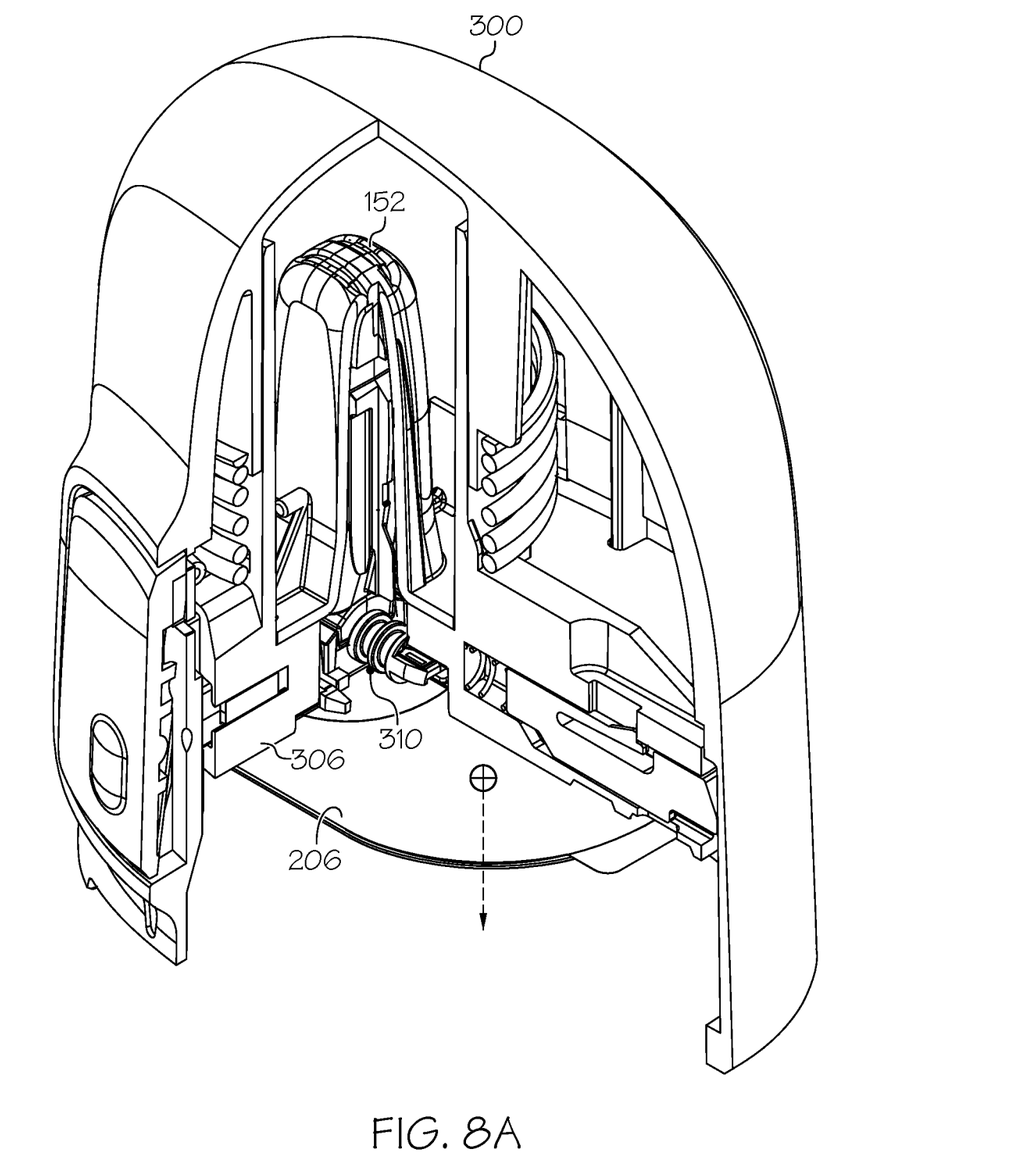
FIG. 8A is a partially cut-away perspective view of the insertion device shown in FIG. 7, in a loaded state.
Figure 8B:
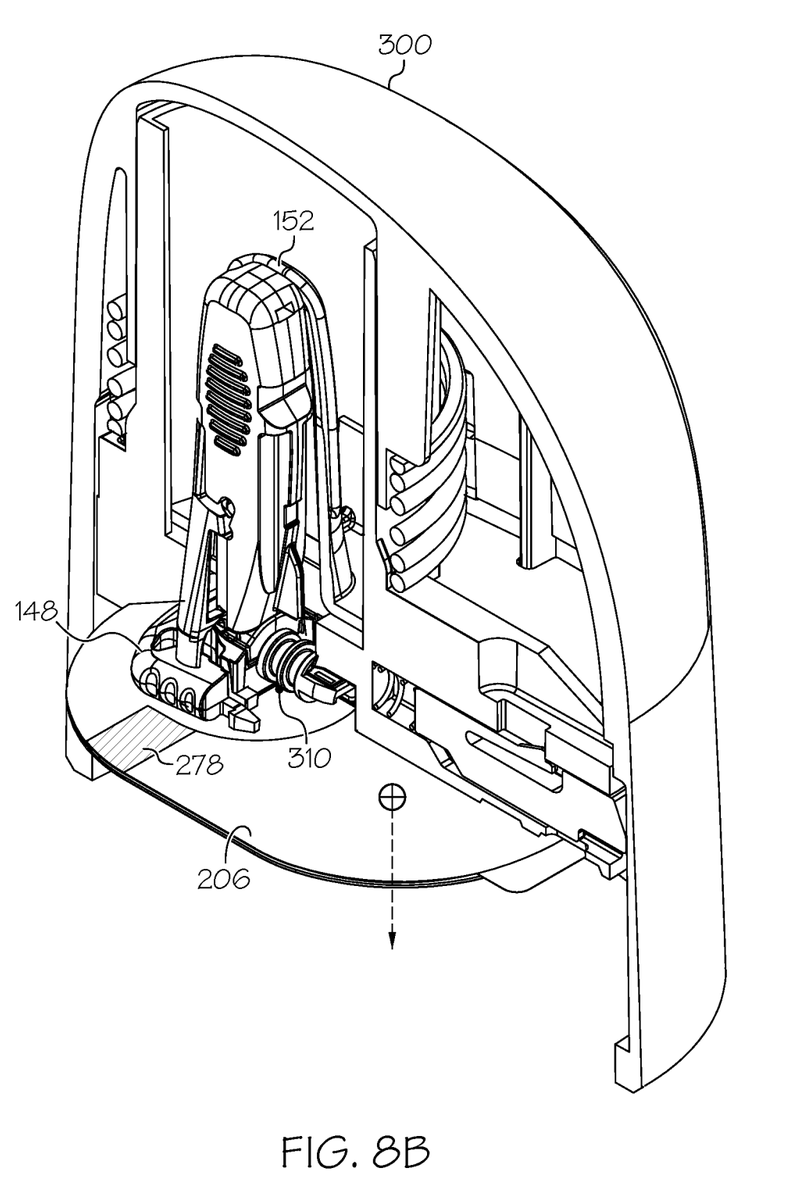
FIG. 8B is another partially cut-away perspective view of the insertion device shown in FIG. 7, in a loaded state.
Figure 9:
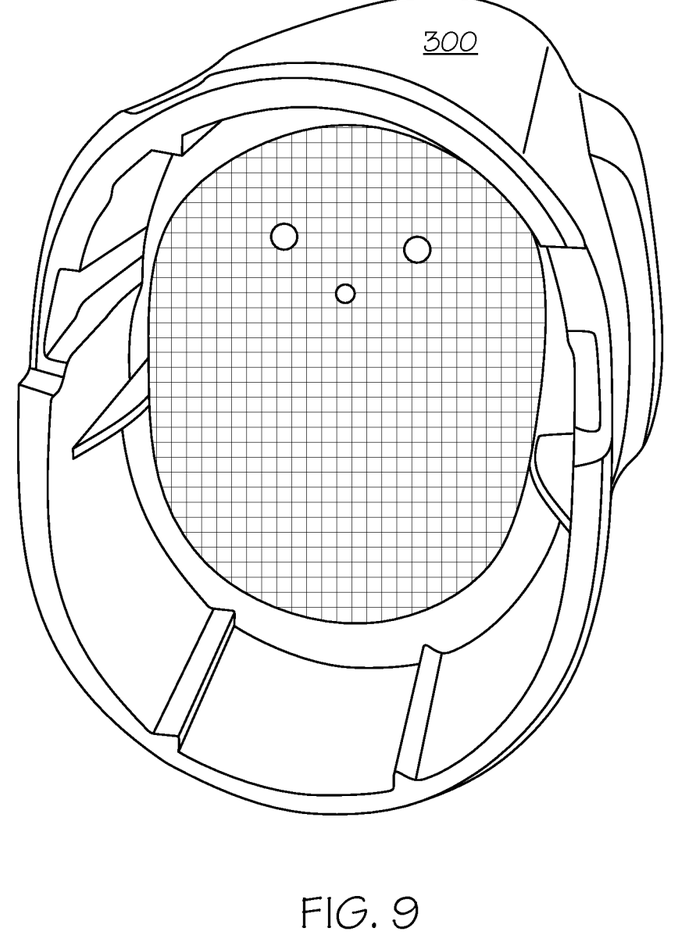
FIG. 9 is a bottom perspective view of the insertion device shown in FIG. 7 in a loaded state.

An exemplary deployment methodology for the glucose sensor 148 will now be described with reference to FIGS. 7-9. FIG. 7 is a perspective view of an insertion device 300 that can be used with the glucose sensor product 140 (see FIG. 2). FIGS. 8A and 8B are partially cut-away views of the insertion device 300 in a loaded state, and FIG. 9 is a bottom perspective view of the insertion device 300 in a loaded state. The insertion device 300 is placed over the glucose sensor product 140 and is pressed down to engage the needle hub assembly 152 and to spring-load the insertion needle. Thereafter, the transport pedestal 142 is separated from the other components of the glucose sensor product 140 by lifting the insertion device 300 away from the transport pedestal 142 while holding down the tabs or "wings" of the pedestal 142 (see FIG. 2). Removal of the transport pedestal 142 causes the backing liner 208 to peel away from the flexible adhesive patch 200 because the backing liner 208 is fixedly attached to the mounting surface 164 of the transport pedestal 142. Accordingly, removal of the transport pedestal 142 exposes the entire adhesive skin-facing side 220 of the flexible adhesive patch 200.

As depicted in FIG. 8A, FIG. 8B, and FIG. 9, the remainder of the glucose sensor product 140 is retained within the interior of the insertion device 300, ready for deployment on the skin of the patient. When in this loaded position, internal supporting structure 306 (shown in FIG. 8A) of the insertion device 300 rests against the two arm sections 278 of the reinforcement liner 206. More specifically, the internal supporting structure 306 of the insertion device 300 contacts the arm sections 278 at or near their distal ends (the contact area for one of the arm sections 278 is shaded in FIG. 8B for reference). The internal supporting structure 306 of the insertion device 300 bears against the arm sections 278 in a manner that prevents the "cantilevered" portion of the reinforcement liner 206 from sagging or bending downward due to removal of the backing liner 208 and due to gravity. FIG. 8A and FIG. 8B include a downward arrow that represents the force associated with gravity and peeling of the backing liner 208, along with a dot that schematically represents an approximate pivot point 310 (near the base of the glucose sensor 148). The downward force creates a moment about the pivot point 310, but the internal supporting structure 306 of the insertion device 300 holds the reinforcement liner 206 in the cantilevered position depicted in FIG. 8A and FIG. 8B. Notably, the stiffness of the reinforcement liner 206 supports the flexible adhesive patch 200, which inhibits drooping, bending, folding, or sagging of the flexible adhesive patch 200 in the downward direction (relative to the orientation of FIG. 8A and FIG. 8B). Consequently, the flexible adhesive patch 200 can be introduced onto the patient's skin in a straight and flat configuration, and in a reliable manner.

Without the presence of the reinforcement liner 206, the soft and pliable nature of the flexible adhesive patch 200 would be prone to bending, folding, or kinking inside the insertion device 300. As described above, the patch 200 is secured to the glucose sensor 148 by way of the sensor-affixing feature 202. Consequently, when held in the position shown in FIG. 8A and FIG. 8B, the force of gravity creates a moment about an axis that is located at or near the sensor-affixing feature 202 (e.g., near the pivot point 310). Referring to FIG. 5, this axis or point of rotation roughly corresponds to an imaginary line between the two arm sections 278 of the reinforcement liner 206. Accordingly, the shape, size, and positioning of the arm sections 278 are selected and designed to counter the effect of the moment created by the cantilevered position of the flexible adhesive patch 200.

After removing the transport pedestal 142 from the assembly, the patient moves the loaded insertion device 300 to the desired insertion location, holds the insertion device 300 against the skin, and actuates the triggering buttons 302 of the insertion device 300 (see FIG. 7). Triggering the insertion device 300 moves the flexible adhesive patch 200 into contact with the patient's skin, and activates the insertion needle to insert the glucose sensor element into the skin. Thereafter, the insertion device 300 is removed and separated from the glucose sensor 148, which remains affixed to the skin by way of the patch 200.

Figure 10:
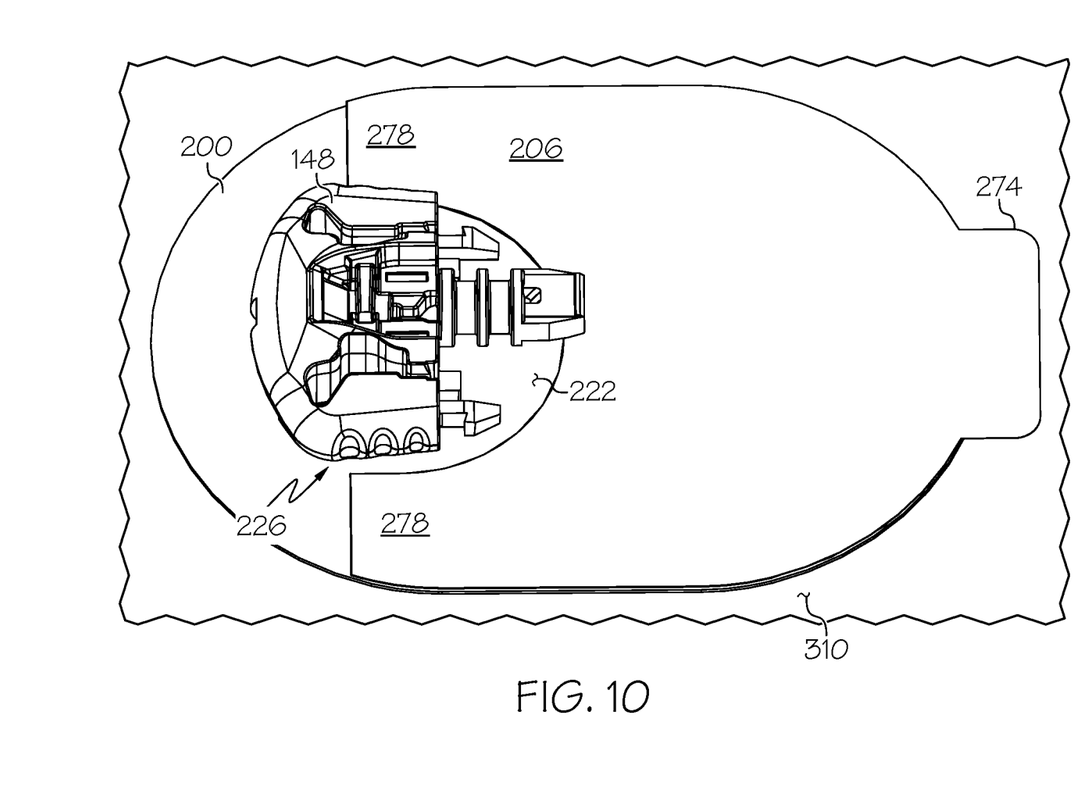
FIG. 10 is a perspective view of a glucose sensor and a reinforcement liner affixed to a flexible adhesive patch, in accordance with an exemplary embodiment.

Next, the needle hub assembly 152 is decoupled and removed from the glucose sensor 148. After removing the needle hub assembly 152, the flexible adhesive patch 200 remains affixed to the skin, and both the glucose sensor 148 and the reinforcement liner 206 are coupled to the component-facing side 222 of the patch 200. In this regard, FIG. 10 is a perspective view that illustrates this particular state of the glucose sensor assembly, as attached to the skin 310. Next, the wireless transmitter 102 can be physically and electrically connected to the glucose sensor 148. The wireless transmitter 102 is connected in this manner before removal of the reinforcement liner 206. In this regard, the reinforcement liner 206 is designed and configured to peel out from under the wireless transmitter 102 so that the wireless transmitter 102 does not get stuck to the adhesive while being connected to the sensor assembly. After connecting the wireless transmitter 102 to the glucose sensor 148, the reinforcement liner 206 is peeled away from the device-affixing feature 204, preferably using the pull tab 274 to initiate the peeling action. Removal of the reinforcement liner 206 exposes the sticky surface of the device-affixing feature 204 (e.g., the second adhesive layer 264) to accommodate placement of the wireless transmitter 102 and adhering to the device-affixing feature 204, resulting in the configuration depicted in FIG. 1. As described previously, the device-affixing feature 204 is designed to be "temporary" to accommodate removal and replacement of the wireless transmitter 102 to the extent needed for recharging, maintenance, or the like.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. An adhesive patch arrangement for a physiological characteristic sensor, the adhesive patch arrangement comprising:
 a flexible adhesive patch comprising an adhesive skin-facing side, and a component-facing side opposite the adhesive skin-facing side;
 a first affixing feature located in a sensor mounting region of the component-facing side of the flexible adhesive patch, the first affixing feature comprising an adhesive sensor-receiving surface to secure the physiological characteristic sensor to the flexible adhesive patch;
 a second affixing feature located in a device mounting region of the component-facing side of the flexible adhesive patch, the second affixing feature comprising an adhesive device-receiving surface to secure a device to the flexible adhesive patch, wherein the sensor mounting region and the device mounting region are distinct and separate regions;
 a removable reinforcement liner adhered to, and covering, the adhesive device-receiving surface of the second affixing feature, the reinforcement liner being shaped to define a cutout area that at least partially surrounds the first affixing feature, and the reinforcement liner being formed from a material that reinforces structural rigidity of the flexible adhesive patch when the reinforcement liner is adhered to the adhesive device-receiving surface; and
 a removable backing liner adhered to, and covering, the adhesive skin-facing side of the flexible adhesive patch.

2. The adhesive patch arrangement of claim 1, further comprising a removable release liner adhered to, and covering, the adhesive sensor-receiving surface of the first affixing feature.

3. The adhesive patch arrangement of claim 2, wherein the removable release liner covers at least a portion of the removable reinforcement liner that defines the cutout area.

4. The adhesive patch arrangement of claim 1, wherein the first affixing feature comprises a double-sided adhesive element.

5. The adhesive patch arrangement of claim 4, wherein the double-sided adhesive element comprises:
 a substrate layer having an upper surface and a lower surface;
 a first adhesive layer on the upper surface of the substrate layer; and
 a second adhesive layer on the lower surface of the substrate layer;

wherein the second adhesive layer couples the substrate layer to the component-facing side of the flexible adhesive patch.

6. The adhesive patch arrangement of claim 1, wherein the second affixing feature comprises a double-sided adhesive element.

7. The adhesive patch arrangement of claim 6, wherein the double-sided adhesive element comprises:
a first adhesive layer coupled to the component-facing side of the flexible adhesive patch; and
a second adhesive layer coupled to the first adhesive layer;
wherein the removable reinforcement liner is adhered to, and covers, the second adhesive layer.

8. The adhesive patch arrangement of claim 1, wherein the removable backing liner includes at least one fold to facilitate peeling removal of the removable backing liner from the adhesive skin-facing side of the flexible adhesive patch.

9. The adhesive patch arrangement of claim 1, wherein the removable reinforcement liner includes a least one fold to facilitate peeling removal of the removable reinforcement liner from the adhesive device-receiving surface of the second affixing feature.

10. The adhesive patch arrangement of claim 1, wherein the removable reinforcement liner has a stiffness measurement that exceeds that of the flexible adhesive patch.

11. A physiological characteristic sensor assembly comprising:
a transport pedestal having a mounting surface;
a backing liner comprising a patch-facing side and a pedestal-facing side opposite the patch-facing side, wherein at least a portion of the pedestal-facing side is attached to the mounting surface of the transport pedestal;
a flexible adhesive patch comprising an adhesive skin-facing side removably adhered to the patch-facing side of the backing liner, and comprising a component-facing side opposite the adhesive skin-facing side;
a first affixing feature located in a sensor mounting region of the component-facing side of the flexible adhesive patch, the first affixing feature comprising an adhesive sensor-receiving surface;
a physiological characteristic sensor coupled to a sensor mounting region of the component-facing side of the flexible adhesive patch, wherein the adhesive sensor-receiving surface of the first affixing feature secures the physiological characteristic sensor to the flexible adhesive patch;
a second affixing feature located in a device mounting region of the component-facing side of the flexible adhesive patch, the second affixing feature comprising an adhesive device-receiving surface to secure a device to the flexible adhesive patch, wherein the sensor mounting region and the device mounting region are distinct and separate regions;
a removable reinforcement liner adhered to, and covering, the adhesive device-receiving surface of the device-affixing feature, the removable reinforcement liner being shaped to define a cutout area that at least partially surrounds the first affixing feature, and the reinforcement liner being formed from a material that reinforces structural rigidity of the flexible adhesive patch when the reinforcement liner is adhered to the adhesive device-receiving surface; and
a removable backing liner adhered to, and covering, the adhesive skin-facing side of the flexible adhesive patch.

12. The physiological characteristic sensor assembly of claim 11, wherein the second affixing feature comprises a double-sided adhesive element.

13. The physiological characteristic sensor assembly of claim 12, wherein the double-sided adhesive element comprises:
a single use adhesive layer coupled to the component-facing side of the flexible adhesive patch; and
a multiple use adhesive layer coupled to the first adhesive layer;
wherein the removable reinforcement liner is adhered to, and covers, the multiple use adhesive layer.

14. The physiological characteristic sensor assembly of claim 11, wherein the backing liner includes at least one fold to facilitate peeling removal of the backing liner from the adhesive skin-facing side of the flexible adhesive patch.

15. The physiological characteristic sensor assembly of claim 11, wherein the removable reinforcement liner includes a least one fold to facilitate peeling removal of the removable reinforcement liner from the adhesive device-receiving surface of the second affixing feature.

16. The physiological characteristic sensor assembly of claim 11, wherein the physiological characteristic sensor comprises a glucose sensor.

17. The physiological characteristic sensor assembly of claim 16, wherein the adhesive device-receiving surface of the second affixing feature is shaped and sized to accommodate a wireless transmitter for the glucose sensor.

18. The physiological characteristic sensor assembly of claim 11, wherein the removable reinforcement liner has a stiffness measurement that exceeds that of the flexible adhesive patch.

19. A physiological characteristic sensor assembly comprising:
a transport pedestal having a primary mounting surface;
an adhesive patch arrangement as recited in claim 1, wherein the removable backing liner of the adhesive patch arrangement is coupled to the primary mounting surface of the transport pedestal; and
a glucose sensor coupled to the flexible adhesive patch of the adhesive patch arrangement by way of the sensor-affixing feature.

20. The physiological characteristic sensor assembly of claim 19, further comprising a needle hub assembly removably coupled to the glucose sensor.

* * * * *